(12) United States Patent
Quisenberry et al.

(10) Patent No.: US 10,272,258 B2
(45) Date of Patent: *Apr. 30, 2019

(54) METHOD AND SYSTEM FOR WOUND CARE

(71) Applicant: ThermoTek, Inc., Flower Mound, TX (US)

(72) Inventors: Tony Quisenberry, Highland Village, TX (US); Todd Davis Taber, Keller, TX (US)

(73) Assignee: ThermoTek, Inc., Flower Mound, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/596,743

(22) Filed: May 16, 2017

(65) Prior Publication Data

US 2017/0246364 A1 Aug. 31, 2017

Related U.S. Application Data

(63) Continuation of application No. 14/537,255, filed on Nov. 10, 2014, now Pat. No. 9,669,233.

(Continued)

(51) Int. Cl.
*A61M 1/00* (2006.01)
*A61M 35/00* (2006.01)
*A61N 5/06* (2006.01)

(52) U.S. Cl.
CPC ......... *A61N 5/0616* (2013.01); *A61M 1/0039* (2013.01); *A61M 1/0084* (2013.01);
(Continued)

(58) Field of Classification Search
CPC .. A61M 1/0088; A61M 1/0084; A61M 35/00; A61M 2205/053; A61M 2205/36;
(Continued)

(56) References Cited

U.S. PATENT DOCUMENTS 773,828 A 11/1904 Titus
2,110,022 A 3/1938 Kliesrath
(Continued)

FOREIGN PATENT DOCUMENTS

CH 670 541 6/1989
DE 35 22 127 1/1987
(Continued)

OTHER PUBLICATIONS

U.S. Appl. No. 12/730,060, Parish et al.
(Continued)

*Primary Examiner* — Theodore Stigell
(74) *Attorney, Agent, or Firm* — Winstead PC

(57) ABSTRACT

In one aspect, the present invention relates to a wound-care assembly The wound-care assembly includes a base layer. A film layer is operatively coupled to the base layer and a fluid conductor is in fluid communication with a wound and a vacuum source. The wound-care assembly further includes a fiber-optic patch comprising a plurality of fiber-optic strands. The fiber-optic strands are pressed into contact with an interior surface of the wound by the fluid conductor. The fiber-optic patch provides ultraviolet light to the wound and the relative vacuum is applied to the wound via the vacuum source and the fluid conductor.

10 Claims, 10 Drawing Sheets

Related U.S. Application Data

(60) Provisional application No. 61/902,455, filed on Nov. 11, 2013.

(52) U.S. Cl.
CPC .......... *A61M 1/0088* (2013.01); *A61M 35/00* (2013.01); *A61M 2202/0208* (2013.01); *A61M 2205/05* (2013.01); *A61M 2205/053* (2013.01); *A61M 2205/36* (2013.01); *A61M 2205/368* (2013.01); *A61N 2005/063* (2013.01); *A61N 2005/0645* (2013.01); *A61N 2005/0661* (2013.01); *A61N 2005/0662* (2013.01)

(58) Field of Classification Search
CPC .......... A61M 2202/0208; A61N 5/0616; A61N 2005/0661; A61N 2005/063
See application file for complete search history.

(56) References Cited

U.S. PATENT DOCUMENTS

| | | |
|---|---|---|
| 2,504,308 A | 4/1950 | Donkle, Jr. |
| 3,014,117 A | 12/1961 | Madding |
| 3,164,152 A | 1/1965 | Vere Nicoll |
| 3,179,106 A | 4/1965 | Meredith |
| 3,345,641 A | 10/1967 | Jennings |
| 3,367,319 A | 2/1968 | Carter, Jr. |
| 3,548,809 A | 12/1970 | Conti Francesco |
| 3,608,091 A | 9/1971 | Olson et al. |
| 3,660,849 A | 5/1972 | Jonnes et al. |
| 3,736,764 A | 6/1973 | Chambers et al. |
| 3,738,702 A | 6/1973 | Jacobs |
| 3,744,053 A | 7/1973 | Parker et al. |
| 3,744,555 A | 7/1973 | Fletcher et al. |
| 3,862,629 A | 1/1975 | Rotta |
| 3,894,213 A | 7/1975 | Agarwala |
| 4,006,604 A | 2/1977 | Seff |
| 4,013,069 A | 3/1977 | Hasty |
| 4,029,087 A | 6/1977 | Dye et al. |
| 4,206,751 A | 6/1980 | Schneider |
| 4,224,941 A | 9/1980 | Stivala |
| 4,375,217 A | 3/1983 | Arkans |
| 4,402,312 A | 9/1983 | Villari et al. |
| 4,419,988 A | 12/1983 | Mummert |
| 4,459,468 A | 7/1984 | Bailey |
| 4,459,822 A | 7/1984 | Pasternack |
| 4,471,787 A | 9/1984 | Bentall |
| 4,503,484 A | 3/1985 | Moxon |
| 4,523,594 A | 6/1985 | Kuznetz |
| 4,547,906 A | 10/1985 | Nishida et al. |
| 4,590,925 A | 5/1986 | Dillon |
| 4,597,384 A | 7/1986 | Whitney |
| 4,608,041 A | 8/1986 | Nielsen |
| D285,821 S | 9/1986 | Kneisley |
| D288,372 S | 2/1987 | Adams |
| 4,660,388 A | 4/1987 | Greene, Jr. |
| 4,738,249 A | 4/1988 | Linman et al. |
| D295,897 S | 5/1988 | Thimm-Kelly |
| 4,741,338 A | 5/1988 | Miyamae |
| 4,795,435 A | 1/1989 | Steer |
| 4,821,354 A | 4/1989 | Little |
| 4,844,072 A | 7/1989 | French et al. |
| 4,884,304 A | 12/1989 | Elkins |
| 4,901,200 A | 2/1990 | Mazura |
| 4,911,231 A | 3/1990 | Horne et al. |
| 4,926,881 A | 5/1990 | Ichinomiya et al. |
| 4,962,761 A | 10/1990 | Golden |
| 4,979,375 A | 10/1990 | Nathans et al. |
| 4,969,881 A | 11/1990 | Viesturs |
| 4,989,589 A | 2/1991 | Pekanmaki et al. |
| 4,995,698 A | 2/1991 | Myers |
| 4,996,970 A | 3/1991 | Legare |
| 5,044,364 A | 9/1991 | Crowther |
| 5,051,562 A | 9/1991 | Bailey et al. |
| D320,872 S | 10/1991 | McCrane |
| 5,062,414 A | 11/1991 | Grim |
| 5,067,040 A | 11/1991 | Fallik |
| 5,080,089 A | 1/1992 | Mason et al. |
| 5,090,409 A | 2/1992 | Genis |
| 5,092,271 A | 3/1992 | Kleinsasser |
| 5,097,829 A | 3/1992 | Quisenberry |
| 5,106,373 A | 4/1992 | Augustine et al. |
| 5,112,045 A | 5/1992 | Mason et al. |
| 5,117,812 A | 6/1992 | McWhorter |
| 5,125,238 A | 6/1992 | Ragan et al. |
| 5,165,127 A | 11/1992 | Nicholson |
| 5,179,941 A | 1/1993 | Siemssen et al. |
| 5,184,612 A | 2/1993 | Augustine |
| 5,186,698 A | 2/1993 | Mason et al. |
| 5,230,335 A | 7/1993 | Johnson, Jr. et al. |
| 5,232,020 A | 8/1993 | Mason et al. |
| 5,241,951 A | 9/1993 | Mason et al. |
| 5,243,706 A | 9/1993 | Frim et al. |
| 5,263,538 A | 11/1993 | Amidieu et al. |
| 5,285,347 A | 2/1994 | Fox et al. |
| D345,082 S | 3/1994 | Wenzl |
| D345,609 S | 3/1994 | Mason et al. |
| D345,802 S | 4/1994 | Mason et al. |
| D345,803 S | 4/1994 | Mason et al. |
| 5,300,101 A | 4/1994 | Augustine et al. |
| 5,300,102 A | 4/1994 | Augustine et al. |
| 5,300,103 A | 4/1994 | Stempel et al. |
| 5,303,716 A | 4/1994 | Mason et al. |
| 5,315,994 A | 5/1994 | Guibert et al. |
| 5,316,250 A | 5/1994 | Mason et al. |
| D348,106 S | 6/1994 | Mason et al. |
| 5,323,847 A | 6/1994 | Koizumi et al. |
| 5,324,319 A | 6/1994 | Mason et al. |
| 5,324,320 A | 6/1994 | Augustine et al. |
| D348,518 S | 7/1994 | Mason et al. |
| 5,330,519 A | 7/1994 | Mason et al. |
| 5,336,250 A | 8/1994 | Augustine |
| 5,343,579 A | 9/1994 | Dickerhoff et al. |
| 5,350,417 A | 9/1994 | Augustine |
| D351,472 S | 10/1994 | Mason et al. |
| 5,352,174 A | 10/1994 | Mason et al. |
| 5,354,117 A | 10/1994 | Danielson et al. |
| D352,781 S | 11/1994 | Mason et al. |
| 5,360,439 A | 11/1994 | Dickerhoff et al. |
| 5,370,178 A | 12/1994 | Agonafer et al. |
| 5,371,665 A | 12/1994 | Quisenberry et al. |
| D354,138 S | 1/1995 | Kelly |
| D357,747 S | 4/1995 | Kelly |
| 5,402,542 A | 4/1995 | Viard |
| 5,405,370 A | 4/1995 | Irani |
| 5,405,371 A | 4/1995 | Augustine et al. |
| 5,407,421 A | 4/1995 | Goldsmith |
| D358,216 S | 5/1995 | Dye |
| 5,411,494 A | 5/1995 | Rodriguez |
| 5,411,541 A | 5/1995 | Bell et al. |
| 5,417,720 A | 5/1995 | Mason |
| 5,440,450 A | 8/1995 | Lau et al. |
| 5,449,379 A | 9/1995 | Hadtke |
| 5,466,250 A | 11/1995 | Johnson, Jr. et al. |
| 5,496,262 A | 3/1996 | Johnson, Jr. et al. |
| 5,496,357 A | 3/1996 | Jensen et al. |
| 5,505,726 A | 4/1996 | Meserol |
| 5,507,792 A | 4/1996 | Mason |
| 5,509,894 A | 4/1996 | Mason et al. |
| 5,514,079 A | 5/1996 | Dillon |
| 5,528,485 A | 6/1996 | Devilbiss et al. |
| 5,561,981 A | 10/1996 | Quisenberry et al. |
| 5,566,062 A | 10/1996 | Quisenberry et al. |
| D376,013 S | 11/1996 | Sandman et al. |
| 5,578,022 A | 11/1996 | Scherson et al. |
| 5,588,954 A | 12/1996 | Ribando et al. |
| 5,591,200 A | 1/1997 | Cone et al. |
| 5,636,643 A | 6/1997 | Argenta et al. |
| D380,874 S | 7/1997 | Caswell |
| 5,645,081 A | 7/1997 | Argenta et al. |
| 5,648,716 A | 7/1997 | Devilbiss et al. |
| D383,546 S | 9/1997 | Amis et al. |
| D383,547 S | 9/1997 | Mason et al. |
| D383,848 S | 9/1997 | Mason et al. |

(56) References Cited

U.S. PATENT DOCUMENTS

| | | |
|---|---|---|
| 5,662,695 A | 9/1997 | Mason et al. |
| 5,669,872 A | 9/1997 | Fox |
| 5,672,152 A | 9/1997 | Mason et al. |
| 5,675,473 A | 10/1997 | McDunn et al. |
| 5,682,748 A | 11/1997 | DeVilbiss et al. |
| 5,689,957 A | 11/1997 | DeVilbiss et al. |
| 5,690,849 A | 11/1997 | DeVilbiss et al. |
| 5,711,029 A | 1/1998 | Visco et al. |
| 5,711,155 A | 1/1998 | DeVilbiss et al. |
| D393,073 S | 3/1998 | Downing et al. |
| 5,731,954 A | 3/1998 | Cheon |
| 5,733,321 A | 3/1998 | Brink |
| D394,707 S | 5/1998 | Tsubooka |
| 5,755,755 A | 5/1998 | Panyard |
| 5,772,618 A | 6/1998 | Mason et al. |
| 5,782,780 A | 7/1998 | Mason et al. |
| 5,795,312 A | 8/1998 | Dye |
| 5,807,294 A | 9/1998 | Cawley et al. |
| 5,827,208 A | 10/1998 | Mason et al. |
| 5,831,824 A | 11/1998 | McDunn et al. |
| D403,779 S | 1/1999 | Davis et al. |
| D404,490 S | 1/1999 | Tripolsky |
| D405,884 S | 2/1999 | Roper |
| 5,865,841 A | 2/1999 | Kolen et al. |
| 5,871,526 A | 2/1999 | Gibbs et al. |
| 5,890,371 A | 4/1999 | Rajasubramanian et al. |
| 5,897,581 A | 4/1999 | Fronda et al. |
| 5,901,037 A | 5/1999 | Hamilton et al. |
| 5,923,533 A | 7/1999 | Olson |
| 5,947,914 A | 9/1999 | Augustine |
| 5,980,561 A | 11/1999 | Kolen et al. |
| 5,989,285 A | 11/1999 | DeVilbiss et al. |
| 6,007,559 A | 12/1999 | Arkans |
| 6,055,157 A | 4/2000 | Bartilson |
| 6,058,010 A | 5/2000 | Schmidt et al. |
| 6,058,712 A | 5/2000 | Rajasubramanian et al. |
| 6,080,120 A | 6/2000 | Sandman et al. |
| D428,153 S | 7/2000 | Davis |
| D430,288 S | 8/2000 | Mason et al. |
| D430,289 S | 8/2000 | Mason et al. |
| 6,117,164 A | 9/2000 | Gildersleeve et al. |
| 6,125,036 A | 9/2000 | Kang et al. |
| 6,129,688 A | 10/2000 | Arkans |
| 6,135,116 A | 10/2000 | Vogel et al. |
| 6,156,059 A | 12/2000 | Olofsson |
| 6,176,869 B1 | 1/2001 | Mason et al. |
| 6,178,562 B1 | 1/2001 | Elkins |
| 6,186,977 B1 | 2/2001 | Andrews et al. |
| 6,231,532 B1 | 5/2001 | Watson et al. |
| 6,235,049 B1 | 5/2001 | Nazerian |
| 6,238,427 B1 | 5/2001 | Matta |
| 6,260,890 B1 | 7/2001 | Mason |
| 6,270,481 B1 | 8/2001 | Mason et al. |
| 6,295,819 B1 | 10/2001 | Mathiprakasam et al. |
| 6,305,180 B1 | 10/2001 | Miller et al. |
| 6,312,453 B1 | 11/2001 | Stefanile et al. |
| 6,319,114 B1 | 11/2001 | Nair et al. |
| 6,352,550 B1 | 3/2002 | Gildersleeve et al. |
| 6,358,219 B1 | 3/2002 | Arkans |
| 6,368,592 B1 | 4/2002 | Colton et al. |
| 6,436,064 B1 | 8/2002 | Kloecker |
| 6,443,978 B1 | 9/2002 | Zharov |
| 6,462,949 B1 | 10/2002 | Parish, IV et al. |
| 6,468,237 B1 | 10/2002 | Lina |
| 6,508,831 B1 | 1/2003 | Kushnir |
| D472,322 S | 3/2003 | Hoglund et al. |
| D473,315 S | 4/2003 | Miros et al. |
| D473,656 S | 4/2003 | Miros et al. |
| D473,948 S | 4/2003 | Elkins et al. |
| 6,551,264 B1 | 4/2003 | Cawley et al. |
| 6,551,347 B1 | 4/2003 | Elkins |
| D474,544 S | 5/2003 | Hoglund et al. |
| 6,562,060 B1 | 5/2003 | Momtaheni |
| 6,596,016 B1 | 7/2003 | Vreman |
| 6,648,904 B2 | 11/2003 | Altshuler et al. |
| D484,601 S | 12/2003 | Griffiths et al. |
| D484,602 S | 12/2003 | Griffiths et al. |
| 6,660,027 B2 | 12/2003 | Gruszecki et al. |
| 6,667,883 B1 | 12/2003 | Solis et al. |
| 6,675,072 B1 | 1/2004 | Kerem |
| D486,870 S | 2/2004 | Mason |
| 6,695,823 B1 | 2/2004 | Lina et al. |
| 6,719,713 B2 | 4/2004 | Mason |
| 6,719,728 B2 | 4/2004 | Mason et al. |
| 6,736,787 B1 | 5/2004 | McEwen et al. |
| D492,411 S | 6/2004 | Bierman |
| 6,775,137 B2 | 8/2004 | Chu et al. |
| D496,108 S | 9/2004 | Machin et al. |
| 6,789,024 B1 | 9/2004 | Kochan, Jr. et al. |
| 6,802,823 B2 | 10/2004 | Mason |
| D499,846 S | 12/2004 | Cesko |
| 6,834,712 B2 | 12/2004 | Parish et al. |
| 6,846,295 B1 | 1/2005 | Ben-Nun |
| 6,848,498 B2 | 2/2005 | Seki et al. |
| 6,855,158 B2 | 2/2005 | Stolpmann |
| 6,893,414 B2 | 5/2005 | Goble et al. |
| D506,553 S | 6/2005 | Tesluk |
| 6,935,409 B1 | 8/2005 | Parish, IV et al. |
| 6,936,019 B2 | 8/2005 | Mason |
| D510,140 S | 9/2005 | Brown |
| 6,945,988 B1 | 9/2005 | Jones |
| D510,626 S | 10/2005 | Krahner et al. |
| D515,218 S | 2/2006 | McGuire et al. |
| 7,004,915 B2 | 2/2006 | Boynton et al. |
| D523,147 S | 6/2006 | Tesluk |
| 7,066,949 B2 | 6/2006 | Gammons et al. |
| 7,081,128 B2 | 7/2006 | Hart et al. |
| D533,668 S | 12/2006 | Brown |
| 7,195,624 B2 | 3/2007 | Lockwood et al. |
| 7,198,046 B1 | 4/2007 | Argenta et al. |
| 7,216,651 B2 | 5/2007 | Argenta et al. |
| D551,351 S | 9/2007 | Silva |
| D551,352 S | 9/2007 | Frangi |
| 7,306,568 B2 | 12/2007 | Diana |
| 7,354,411 B2 | 4/2008 | Perry et al. |
| D568,482 S | 5/2008 | Gramza et al. |
| D569,985 S | 5/2008 | Ganapathy et al. |
| 7,427,153 B1 | 9/2008 | Jacobs et al. |
| 7,429,252 B2 | 9/2008 | Sarangapani |
| 7,484,552 B2 | 2/2009 | Pfahnl |
| 7,492,252 B2 | 2/2009 | Maruyama |
| 7,524,286 B2 | 4/2009 | Johnson |
| 7,532,953 B2 | 5/2009 | Vogel |
| 7,553,306 B1 | 6/2009 | Hunt et al. |
| D595,620 S | 7/2009 | Kingsbury |
| D601,707 S | 10/2009 | Chouiller |
| 7,608,066 B2 | 10/2009 | Vogel |
| 7,618,382 B2 | 11/2009 | Vogel et al. |
| D608,006 S | 1/2010 | Avitable et al. |
| D612,947 S | 3/2010 | Turtzo et al. |
| D613,870 S | 4/2010 | Shust |
| 7,717,869 B2 | 5/2010 | Eischen, Sr. |
| D618,358 S | 6/2010 | Avitable et al. |
| D619,267 S | 7/2010 | Beckwith et al. |
| D620,122 S | 7/2010 | Cotton |
| 7,763,000 B2 | 7/2010 | Risk, Jr. et al. |
| 7,799,004 B2 | 9/2010 | Tumey |
| 7,804,686 B2 | 9/2010 | Parish et al. |
| D625,018 S | 10/2010 | Smith et al. |
| D626,241 S | 10/2010 | Sagnip et al. |
| D626,242 S | 10/2010 | Sagnip et al. |
| D626,243 S | 10/2010 | Sagnip et al. |
| D626,245 S | 10/2010 | Sagnip et al. |
| 7,811,269 B2 | 10/2010 | Boynton et al. |
| D627,896 S | 11/2010 | Matsuo et al. |
| D628,300 S | 11/2010 | Caden |
| 7,837,673 B2 | 11/2010 | Vogel |
| D630,759 S | 1/2011 | Matsuo et al. |
| 7,867,206 B2 | 1/2011 | Lockwood et al. |
| 7,871,387 B2 | 1/2011 | Tordella et al. |
| D631,971 S | 2/2011 | Turtzo et al. |
| D633,657 S | 3/2011 | Oban |
| D634,437 S | 3/2011 | Gramza et al. |
| D634,851 S | 3/2011 | Chiang |

(56) References Cited

U.S. PATENT DOCUMENTS

| | | |
|---|---|---|
| D635,266 S | 3/2011 | Chiang |
| D635,267 S | 3/2011 | Chiang |
| 7,896,864 B2 | 3/2011 | Lockwood et al. |
| 7,896,910 B2 | 3/2011 | Schirrmacher et al. |
| 7,909,861 B2 | 3/2011 | Balachandran et al. |
| D636,497 S | 4/2011 | Giaccone |
| D638,950 S | 5/2011 | Janzon |
| D640,381 S | 6/2011 | Tweardy et al. |
| 7,959,588 B1 | 6/2011 | Wolpa |
| 8,007,491 B2 | 8/2011 | Pinto et al. |
| D649,648 S | 11/2011 | Cavalieri et al. |
| 8,052,630 B2 | 11/2011 | Kloecker et al. |
| 8,084,663 B2 | 12/2011 | Watson, Jr. |
| 8,088,113 B2 | 1/2012 | Scherson et al. |
| 8,100,956 B2 | 1/2012 | Quisenberry et al. |
| 8,109,981 B2 | 2/2012 | Gertner et al. |
| D655,420 S | 3/2012 | Bowles |
| D655,821 S | 3/2012 | Matsuo |
| 8,128,672 B2 | 3/2012 | Quisenberry et al. |
| 8,142,486 B2 | 3/2012 | Quisenberry et al. |
| D657,063 S | 4/2012 | Chiang |
| 8,157,792 B2 | 4/2012 | Dolliver et al. |
| D660,438 S | 5/2012 | Kennedy et al. |
| D660,439 S | 5/2012 | Chen et al. |
| D662,212 S | 6/2012 | Quisenberry |
| D662,213 S | 6/2012 | Quisenberry |
| D662,214 S | 6/2012 | Quisenberry |
| 8,202,262 B2 | 6/2012 | Lina et al. |
| D663,850 S | 7/2012 | Joseph |
| D664,260 S | 7/2012 | Quisenberry |
| D665,088 S | 8/2012 | Joseph |
| D665,470 S | 8/2012 | Galbraith |
| D666,258 S | 8/2012 | Campbell |
| D666,301 S | 8/2012 | Joseph |
| 8,240,885 B2 | 8/2012 | Miller |
| 8,248,798 B2 | 8/2012 | Parish et al. |
| D679,023 S | 3/2013 | Quisenberry |
| 8,425,580 B2 | 4/2013 | Quisenberry et al. |
| D683,042 S | 5/2013 | Quisenberry |
| 8,444,581 B1 | 5/2013 | Maxon-Maldonado et al. |
| 8,449,483 B2 | 5/2013 | Eddy |
| 8,485,995 B1 | 7/2013 | Maxon-Maldonado |
| 8,529,613 B2 | 9/2013 | Radziunas et al. |
| 8,569,566 B2 | 10/2013 | Blott et al. |
| 8,574,278 B2 | 11/2013 | Quisenberry |
| 8,632,576 B2 | 1/2014 | Quisenberry |
| 8,753,300 B2 | 6/2014 | Deshpande |
| 8,753,383 B2 | 6/2014 | Parish et al. |
| 8,758,419 B1 | 6/2014 | Quisenberry et al. |
| 8,772,567 B2 | 7/2014 | Eckstein et al. |
| 8,778,005 B2 | 7/2014 | Parish et al. |
| 8,827,935 B2 | 9/2014 | Maxon-Maldonado |
| 8,834,393 B2 | 9/2014 | Maxon-Maldonado et al. |
| 8,940,034 B2 | 1/2015 | Quisenberry |
| 9,101,463 B2 | 8/2015 | Stormby |
| 9,114,055 B2 | 8/2015 | Edelman et al. |
| 9,119,705 B2 | 9/2015 | Parish et al. |
| 9,132,057 B2 | 9/2015 | Wilford et al. |
| 9,180,041 B2 | 11/2015 | Parish et al. |
| 9,192,539 B2 | 11/2015 | Parish et al. |
| 9,669,233 B2 * | 6/2017 | Quisenberry ........ A61N 5/0616 |
| 2001/0018604 A1 | 8/2001 | Elkins |
| 2001/0039439 A1 | 11/2001 | Elkins et al. |
| 2002/0116041 A1 | 8/2002 | Daoud |
| 2002/0143373 A1 | 10/2002 | Courtnage et al. |
| 2003/0050594 A1 | 3/2003 | Zamierowski |
| 2003/0083610 A1 | 5/2003 | McGrath et al. |
| 2003/0089486 A1 | 5/2003 | Parish et al. |
| 2003/0089487 A1 | 5/2003 | Parish, IV et al. |
| 2003/0125649 A1 | 7/2003 | McIntosh et al. |
| 2003/0127215 A1 | 7/2003 | Parish, IV et al. |
| 2003/0135252 A1 | 7/2003 | MacHold et al. |
| 2003/0139255 A1 | 7/2003 | Lina |
| 2003/0163183 A1 | 8/2003 | Carson |
| 2003/0171703 A1 | 9/2003 | Grim et al. |
| 2003/0176822 A1 | 9/2003 | Morgenlander |
| 2003/0191437 A1 | 10/2003 | Knighton et al. |
| 2004/0008483 A1 | 1/2004 | Cheon |
| 2004/0030281 A1 | 2/2004 | Goble et al. |
| 2004/0046108 A1 | 3/2004 | Spector |
| 2004/0054307 A1 | 3/2004 | Mason et al. |
| 2004/0068309 A1 | 4/2004 | Edelman |
| 2004/0068310 A1 | 4/2004 | Edelman |
| 2004/0099407 A1 | 5/2004 | Parish, IV et al. |
| 2004/0133135 A1 | 7/2004 | Diana |
| 2004/0176805 A1 | 9/2004 | Whelan et al. |
| 2004/0186535 A1 | 9/2004 | Knowlton |
| 2004/0193218 A1 | 9/2004 | Butler |
| 2004/0210176 A1 | 10/2004 | Diana |
| 2004/0221604 A1 | 11/2004 | Ota et al. |
| 2004/0260231 A1 | 12/2004 | Goble et al. |
| 2005/0004636 A1 | 1/2005 | Noda et al. |
| 2005/0006061 A1 | 1/2005 | Quisenberry et al. |
| 2005/0033390 A1 | 2/2005 | McConnell |
| 2005/0039887 A1 | 2/2005 | Parish, IV et al. |
| 2005/0070828 A1 | 3/2005 | Hampson et al. |
| 2005/0070835 A1 | 3/2005 | Joshi |
| 2005/0080465 A1 | 4/2005 | Zelickson et al. |
| 2005/0126578 A1 | 6/2005 | Garrison et al. |
| 2005/0133214 A1 | 6/2005 | Pfahnl |
| 2005/0143797 A1 | 6/2005 | Parish et al. |
| 2005/0177093 A1 | 8/2005 | Barry et al. |
| 2005/0182364 A1 | 8/2005 | Burchman |
| 2005/0187500 A1 | 8/2005 | Perry et al. |
| 2005/0256556 A1 | 11/2005 | Schirrmacher et al. |
| 2005/0274120 A1 | 12/2005 | Quisenberry et al. |
| 2005/0284615 A1 | 12/2005 | Parish et al. |
| 2006/0034053 A1 | 2/2006 | Parish et al. |
| 2006/0058714 A1 | 3/2006 | Rhoades |
| 2006/0116620 A1 | 6/2006 | Oyaski |
| 2006/0167531 A1 | 7/2006 | Gertner et al. |
| 2006/0217787 A1 * | 9/2006 | Olson ............... A61N 5/0616 607/88 |
| 2006/0241549 A1 | 10/2006 | Sunnen |
| 2006/0253089 A1 | 11/2006 | Lin |
| 2006/0276845 A1 | 12/2006 | George et al. |
| 2006/0282028 A1 * | 12/2006 | Howard ............. A61M 27/00 602/2 |
| 2007/0032778 A1 | 2/2007 | Heaton et al. |
| 2007/0068651 A1 | 3/2007 | Gammons et al. |
| 2007/0112401 A1 | 5/2007 | Balachandran et al. |
| 2007/0118194 A1 | 5/2007 | Mason et al. |
| 2007/0129658 A1 | 6/2007 | Hampson et al. |
| 2007/0233209 A1 | 10/2007 | Whitehurst |
| 2007/0260162 A1 | 11/2007 | Meyer et al. |
| 2007/0282249 A1 | 12/2007 | Quisenberry |
| 2008/0058911 A1 | 3/2008 | Parish et al. |
| 2008/0064992 A1 | 3/2008 | Stewart et al. |
| 2008/0071330 A1 | 3/2008 | Quisenberry |
| 2008/0082029 A1 | 4/2008 | Diana |
| 2008/0103397 A1 | 5/2008 | Barak |
| 2008/0103422 A1 | 5/2008 | Perry et al. |
| 2008/0125775 A1 | 5/2008 | Morris |
| 2008/0132816 A1 | 6/2008 | Kane et al. |
| 2008/0132976 A1 | 6/2008 | Kane et al. |
| 2008/0249559 A1 | 10/2008 | Brown et al. |
| 2008/0262399 A1 | 10/2008 | Kovelman et al. |
| 2008/0319362 A1 | 12/2008 | Joseph |
| 2009/0069731 A1 | 3/2009 | Parish et al. |
| 2009/0109622 A1 | 4/2009 | Parish et al. |
| 2009/0149821 A1 | 6/2009 | Scherson et al. |
| 2009/0237264 A1 | 9/2009 | Bobey |
| 2009/0254159 A1 | 10/2009 | Stormby |
| 2009/0254160 A1 | 10/2009 | Shawver et al. |
| 2010/0010477 A1 | 1/2010 | Augustine et al. |
| 2010/0030306 A1 | 2/2010 | Edelman et al. |
| 2010/0081975 A1 | 4/2010 | Avitable et al. |
| 2010/0121230 A1 | 5/2010 | Vogel et al. |
| 2010/0137764 A1 | 6/2010 | Eddy |
| 2010/0145421 A1 | 6/2010 | Tomlinson et al. |
| 2010/0150991 A1 | 6/2010 | Bernstein |
| 2010/0160838 A1 * | 6/2010 | Krespi ............. A61B 18/26 601/15 |

(56) References Cited

U.S. PATENT DOCUMENTS

| | | | |
|---|---|---|---|
| 2010/0179469 A1* | 7/2010 | Hammond | A61N 5/0603 604/20 |
| 2010/0186436 A1 | 7/2010 | Stormby | |
| 2010/0210982 A1 | 8/2010 | Balachandran et al. | |
| 2010/0249679 A1 | 9/2010 | Perry et al. | |
| 2010/0249680 A1 | 9/2010 | Davis | |
| 2011/0009785 A1 | 1/2011 | Meyer et al. | |
| 2011/0034861 A1 | 2/2011 | Schaefer | |
| 2011/0037002 A1 | 2/2011 | Johnson et al. | |
| 2011/0071447 A1 | 3/2011 | Liu et al. | |
| 2011/0082401 A1 | 4/2011 | Iker et al. | |
| 2011/0087142 A1 | 4/2011 | Ravikumar et al. | |
| 2011/0275983 A1 | 11/2011 | Quisenberry et al. | |
| 2011/0282269 A1 | 11/2011 | Quisenberry et al. | |
| 2012/0041526 A1 | 2/2012 | Stormby | |
| 2012/0130457 A1 | 5/2012 | Gammons et al. | |
| 2012/0259266 A1* | 10/2012 | Quisenberry | A61F 7/02 604/20 |
| 2012/0289885 A1* | 11/2012 | Cottrell | A61N 5/0616 604/20 |
| 2013/0030331 A1 | 1/2013 | Quisenberry et al. | |
| 2013/0103123 A1* | 4/2013 | Khan | A61N 5/0624 607/90 |
| 2013/0116612 A1* | 5/2013 | Stephan | A61N 5/06 602/43 |
| 2013/0191437 A1 | 7/2013 | Itoh | |
| 2013/0216627 A1 | 8/2013 | Galbraith et al. | |
| 2013/0245508 A1 | 9/2013 | Maxon-Maldonado | |
| 2013/0245519 A1 | 9/2013 | Edelman et al. | |
| 2013/0253383 A1 | 9/2013 | Maxon-Maldonado | |
| 2013/0261512 A1 | 10/2013 | Maxon-Maldonado et al. | |
| 2013/0281947 A1 | 10/2013 | Quisenberry | |
| 2013/0331767 A1 | 12/2013 | Quisenberry | |
| 2014/0012169 A1 | 1/2014 | Wilford et al. | |
| 2014/0046410 A1 | 2/2014 | Wyatt | |
| 2014/0052054 A1 | 2/2014 | Quisenberry | |
| 2014/0236271 A1 | 8/2014 | Fronda et al. | |
| 2014/0257175 A1 | 9/2014 | Quisenberry | |
| 2014/0316330 A1 | 10/2014 | Fudem et al. | |
| 2014/0323949 A1 | 10/2014 | Quisenberry | |
| 2015/0133849 A1 | 5/2015 | Quisenberry et al. | |
| 2015/0290364 A1 | 10/2015 | Wall et al. | |
| 2015/0328042 A1 | 11/2015 | Parish et al. | |
| 2016/0030236 A1 | 2/2016 | Parish et al. | |
| 2016/0067104 A1 | 3/2016 | Sarangapani et al. | |
| 2016/0082238 A1 | 3/2016 | Wells et al. | |
| 2016/0317348 A1 | 11/2016 | Banker | |
| 2017/0119940 A1 | 5/2017 | Quisenberry | |

FOREIGN PATENT DOCUMENTS

| | | |
|---|---|---|
| EP | 0076074 A1 | 4/1983 |
| EP | 0 489 326 | 6/1992 |
| GB | 2373444 A | 9/2002 |
| JP | 2009504246 A | 2/2009 |
| SU | 689674 | 10/1979 |
| WO | WO-1989009583 A2 | 10/1989 |
| WO | WO-93/09727 | 5/1993 |
| WO | WO-93/12708 A2 | 7/1993 |
| WO | WO-1996005873 A1 | 2/1996 |
| WO | WO-9807397 A1 | 2/1998 |
| WO | WO-1998016176 A1 | 4/1998 |
| WO | WO-00/40186 | 7/2000 |
| WO | WO-01/14012 A1 | 3/2001 |
| WO | WO-01/54635 A1 | 8/2001 |
| WO | WO-2004105676 A1 | 12/2004 |
| WO | WO-2005046760 A1 | 5/2005 |
| WO | WO-2007019038 A2 | 2/2007 |
| WO | WO-2008099017 A1 | 8/2008 |
| WO | WO-2010124234 A1 | 10/2010 |
| WO | WO-2012067918 A1 | 5/2012 |

OTHER PUBLICATIONS

U.S. Appl. No. 12/708,422, Balachandran et al.
U.S. Appl. No. 12/871,188, Parish et al.
U.S. Appl. No. 13/107,264, Quisenberry.
U.S. Appl. No. 12/364,434, Quisenberry.
U.S. Appl. No. 13/190,564, Quisenberry et al.
U.S. Appl. No. 29/397,856, Quisenberry.
U.S. Appl. No. 29/400,194, Quisenberry.
U.S. Appl. No. 29/400,202, Quisenberry.
U.S. Appl. No. 29/400,212, Quisenberry.
U.S. Appl. No. 29/402,115, Quisenberry.
U.S. Appl. No. 13/796,139, Quisenberry.
U.S. Appl. No. 13/962,994, Quisenberry.
U.S. Appl. No. 14/062,428, Quisenberry.
U.S. Appl. No. 14/197,324, Quisenberry.
U.S. Appl. No. 15/227,417, filed Aug. 3, 2016, Overton et al.
U.S. Appl. No. 15/370,689, Quisenberry.
Artikis, T., PCT International Preliminary Report on Patentability dated Jul. 29, 2005, (10 pgs.).
Tom Lee, T.Y. et al; "Compact Liquid Cooling System for Small, Moveable Electronic Equipment", IEEE Transactions on Components, Hybrids, and Manufacturing Technology, Oct. 15, 1992, vol. 15, No. 5, pp. 786-793.
Copenheaver, Blaine R., "International Search Report" for PCT/US2007/022148 dated Apr. 2, 2008, 2 pages.
Young, Lee W., "International Search Report" for PCT/US07/08807 dated Mar. 3, 2008, (3 pages).
Mahmoud Karimi Azar Daryany, et al., "Photoinactivation of *Escherichia coli* and *Saccharomyces cerevisiae* Suspended in Phosphate-Buffered Saline-A Using 266- and 355-nm Pulsed Ultraviolet Light", Curr Microbiol, vol. 56, 2008, pp. 423-428.
J. Li, et al., "Enhanced germicidal effects of pulsed UV-LED irradiation on biofilms", Journal of Applied Microbiology, 2010, pp. 1-8.
Cyro/Temp Therapy Systems; Product News Catalogue; Jobst Institute, Inc., 6 pages (Copyright 1982).
Quisenberry, Tony, "U.S. Appl. No. 13/359,210" filed Jan. 26, 2012.
Quisenberry, Tony, "U.S. Appl. No. 29/424,860" filed Jun. 15, 2012.
Quisenberry, Tony, "U.S. Appl. No. 13/456,410" filed Apr. 26, 2012.
Copenheaver, Blaine R., "International Search Report" for PCT/US2012/035096 as dated Aug. 7, 2012, 3 pages.
Quisenberry, Tony, "U.S. Appl. No. 13/558,615" filed Jul. 26, 2012.
Copenheaver, Blaine R., "International Search Report" prepared for PCT/US2013/030475 dated May 23, 2013, 3 pages.
Young, Lee W., International Search Report of PCT Application No. PCT/US2014/64805, dated Mar. 13, 2015 (3 pages).
Hair Science Systems LLC, "Hair Science Systems—01 mobile unit--", Hair Saver Chemo Cold Cap, www.hairsciencesystems.com, 2 pages.
"U.S. FDA de novo clearance for the DigniCap® scalp cooling system that reduces hair loss related to chemotherapy for women with breast cancer", www.sysmex-europe.com/company/news-and-events/press-releases, accessed on Jun. 17, 2016, 3 pages.
"DigniLife—Prevention of Chermotherapy-Induced Alopecia", www.sysmex.co.uk/products/oncology/scalp-cooling-system-dignilife, accessed on Jun. 17, 2016, 3 pages.

* cited by examiner

METHOD AND SYSTEM FOR WOUND CARE

CROSS-REFERENCE TO RELATED APPLICATIONS

This application is a continuation of U.S. patent application Ser. No. 14/537,255, filed on Nov. 2, 2014 (now U.S. Pat. No. 9,669,233). U.S. patent application Ser. No. 14/537,255 claims priority to U.S. Provisional Patent Application No. 61/902,455, filed Nov. 11, 2013. U.S. patent application Ser. No. 14/537,255 and U.S. Provisional Patent Application No. 61/902,455 are each incorporated herein by reference.

BACKGROUND

Field of the Invention

The present invention relates to a wound care method and system with one or both of vacuum-light therapy, pulsed radio frequency ("RF"), and oxygenation, and more particularly, but not by way of limitation, to adaptive wound-care patch capable of being utilized in a variety of wound locations where one or both of vacuum-light therapy, pulsed radio frequency ("RF"), and oxygenation may be applied thereto.

History of the Related Art

An important aspect of patient treatment is wound care. Medical facilities are constantly in need of advanced technology for the cleaning and treatment of skin wounds. The larger the skin wound, the more serious the issues are of wound closure and infection prevention. The rapidity of the migration over the wound of epithelial and subcutaneous tissue adjacent the wound is thus critical. Devices have been developed and/or technically described which address certain aspects of such wound healing. For example, U.S. Pat. No. 6,695,823 to Lina et al. ("Lina") describes a wound therapy device that facilitates wound closure. A vacuum pump is taught for collecting fluids from the wound. WO 93/09727 discloses a solution for wound drainage by utilizing negative pressure over the wound to promote the above references migration of epithelial and subcutaneous tissue over the wound.

In other embodiments, wound treatment is performed using light therapy. For example, U.S. Pat. No. 7,081,128 to Hart et al. ("Hart") describes a method of treating various medical conditions such as, for example, joint inflammation, edema, etc., utilizing an array of Light Emitting Diodes contained on a flexible substrate that may be wrapped around an anatomical feature of the human body. U.S. Pat. No. 6,596,016 to Vreman et al. ("Vreman") discloses a phototherapy garment for an infant having a flexible backing material, a transparent liner, and a flexible printed circuit sheet containing surface-mounted LEDs. The LEDs preferably emit high-intensity blue light, suitable for the treatment of neonatal hyperbilirubinemia. The device may include a portable power supply.

In other embodiments, wound treatment is performed using oxygen. The use of oxygen for the treatment of skin wounds has been determined to be very beneficial in certain medical instances. The advantages are multitudinous and include rapidity in healing. For this reason, systems have been designed for supplying high concentration of oxygen to wound sites to facilitate the healing process. For example, U.S. Pat. No. 5,578,022 to Scherson et al. ("Scherson") teaches an oxygen producing bandage and method. One of the benefits cited in Scherson is the ability to modulate a supply of concentrated hyperbaric oxygen to skin wounds. Although oxygen is beneficial in direct application of pre-determined dosages to skin wounds, too much oxygen can be problematic. Oxygen applied to a wound site can induce the growth of blood vessels for stimulating the growth of new skin. Too much oxygen, however, can lead to toxic effects and the cessation of healing of the wound. It would be an advantage, therefore, to maximize the effectiveness of oxygen applied to a wound area by enhancing the absorption rate of oxygen into the skin and tissue fluids. By enhancing the absorption rate of the oxygen in the wound, less exposure time and concomitantly fewer toxic side effects to the endothelial cells surrounding the wound, such as devasculation, occurs. It would be a further advantage, therefore, to utilize existing medical treatment modalities directed toward other aspects of patient therapy to augment oxygenation for wound care.

SUMMARY

The present invention relates generally to a wound care method and system with one or both of vacuum-light therapy, pulsed radio frequency ("RF"), and oxygenation, and more particularly, but not by way of limitation, to adaptive wound-care patch capable of being utilized in a variety of wound locations where one or both of vacuum-light therapy, pulsed radio frequency ("RF"), and oxygenation may be applied thereto.

In one aspect, the present invention relates to a wound-care assembly The wound-care assembly includes a base layer. A film layer is operatively coupled to the base layer and a fluid conductor is in fluid communication with a wound and a vacuum source. The wound-care assembly further includes a fiber-optic patch comprising a plurality of fiber-optic strands. The fiber-optic strands are pressed into contact with an interior surface of the wound by the fluid conductor. The fiber-optic patch provides ultraviolet light to the wound and the relative vacuum is applied to the wound via the vacuum source and the fluid conductor.

In another aspect, the present invention relates to a method of utilizing a wound-care assembly. The method includes applying a fiber-optic patch to a wound. The fiber-optic patch is pressed into contact with an inner surface of the wound via a fluid conductor. The fluid conductor and the fiber-optic patch are secured to the wound. A vacuum applicator is applied to and secured to the fluid conductor. Ultraviolet light is applied to the wound via the fiber-optic patch and a relative vacuum is applied to the wound via the fluid conductor.

BRIEF DESCRIPTION OF THE DRAWINGS

For a more complete understanding of the present invention and for further objects and advantages thereof, reference may now be had to the following description taken in conjunction with the accompanying drawings in which.

DETAILED DESCRIPTION

Figure 1A:
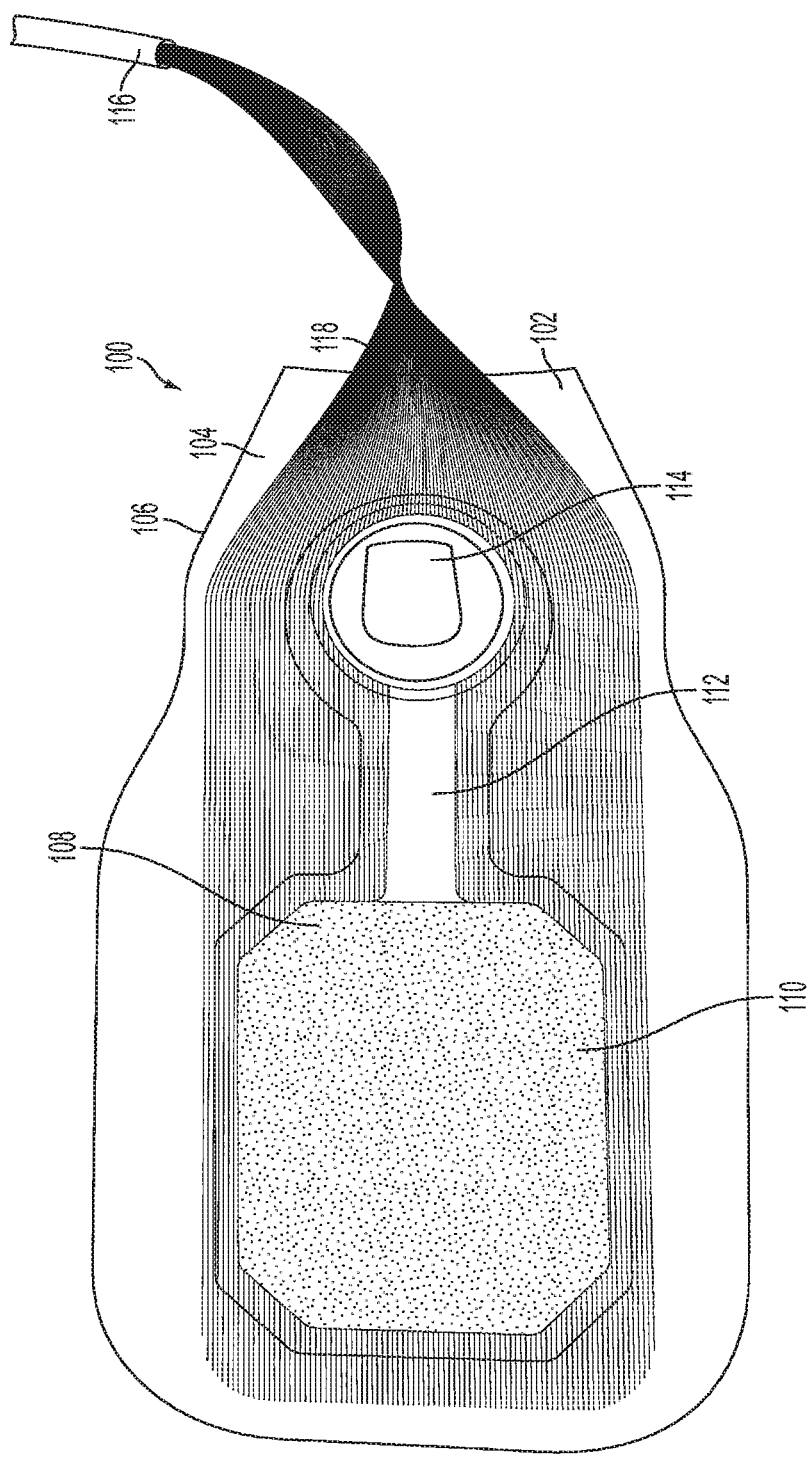
FIG. 1A is a top view of a wound-care patch according to an exemplary embodiment.

Various embodiments of the present invention will now be described more fully with reference to the accompanying drawings. The invention may, however, be embodied in many different forms and should not be construed as limited to the embodiments set forth herein.

FIG. 1 is a top view of a wound-care patch 100. The wound-care patch 100 includes a base layer 102 that is coupled to a film layer 104. In a typical embodiment, the base layer 102 is constructed of a sterile, ethylyne-oxide, biocompatible material. The film layer 104 is, in a typical embodiment, constructed from, for example, medical grade polyurethane. A peripheral edge 106 of the film layer 104 is secured to a corresponding edge of the base layer 102 through a process such as, for example, welding. Connection of the film layer 104 to the base layer 102 creates a seal around the peripheral edge 106, which seal prevents leakage of fluid therefrom. A fluid port 114 is formed in the film layer 104.

Still referring to FIG. 1, a fluid conductor 108 is disposed between the base layer 102 and the film layer 104. In a typical embodiment, the fluid conductor 108 is flexible, absorptive, and constructed of, for example, medical grade foam. The fluid conductor includes a wound-treatment portion 110 disposed proximate a wound (not shown in FIG. 1) and a straw portion 112 that fluidly couples the wound-treatment portion 110 to the fluid port 114. In a typical embodiment, the fluid conductor 108 transmits fluids such as, for example, liquids or gases, from the wound to the fluid port 114 and, thus, allows a vacuum to be applied to the wound via the fluid port 114. In addition, the straw portion 112 facilitates placement of the fluid port 114 at a location removed from the wound. Such an arrangement is beneficial if, for example, space constraints do not allow the fluid port 114 to be placed near the wound.

Still referring to FIG. 1, a fiber-optic cable 116 is coupled to the wound-care patch 100. A plurality of fiber-optic strands 118 extend from the fiber-optic cable 116. The fiber-optic strands are disposed between the base layer 102 and the film layer 104 and are arranged in a generally flat, side-by-side configuration. The fiber-optic strands 118 are disposed beneath the fluid conductor 108.

Figure 1B:
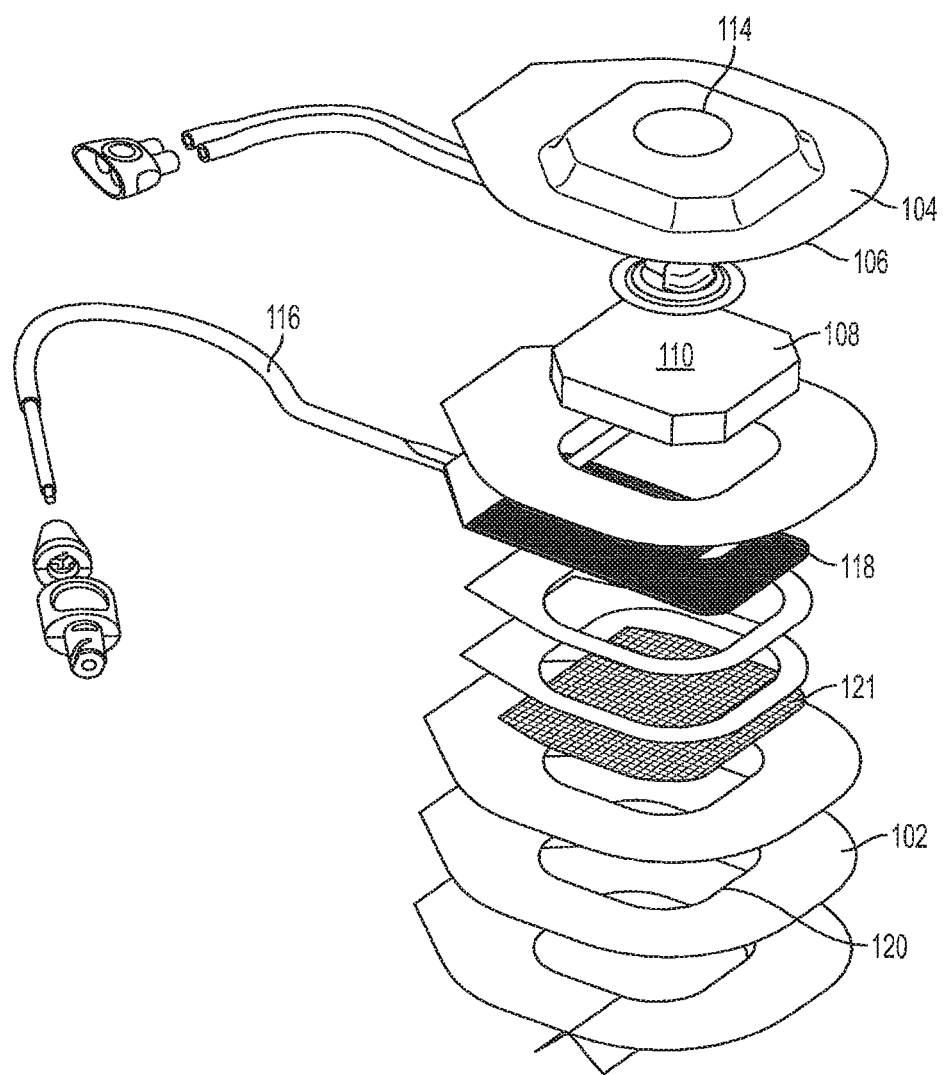
FIG. 1B is an exploded view of the wound-care patch of FIG. 1A according to an exemplary embodiment.
Figure 1C:
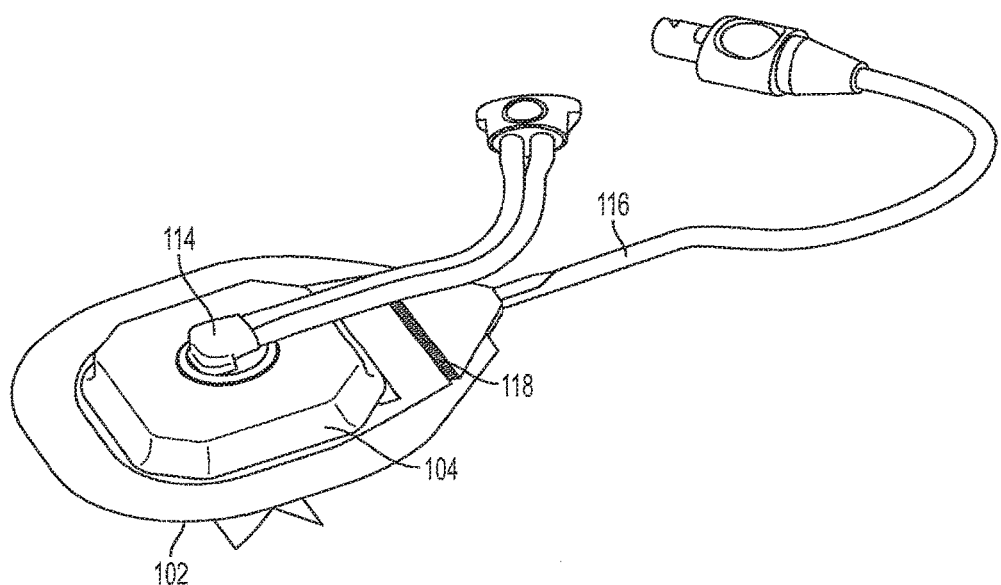
FIG. 1C is a perspective view of the wound-care patch of FIG. 1A according to an exemplary embodiment.
Figure 2:
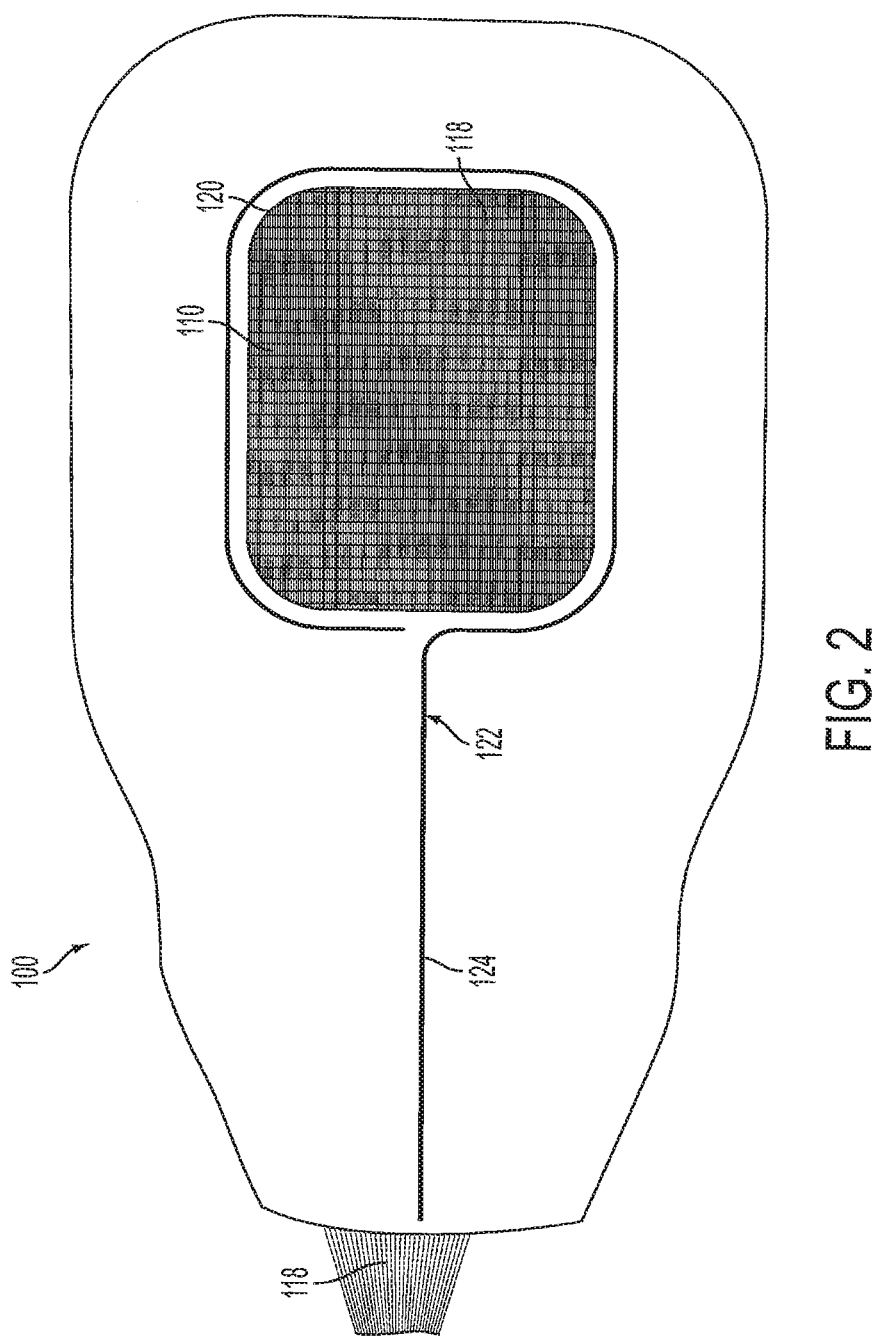
FIG. 2 is a bottom view of the wound-care patch of FIG. 1 according to an exemplary embodiment.

FIG. 1B is an exploded view of the wound-care patch 100. FIG. 1C is a perspective view of the wound-care patch 100. FIG. 2 is a bottom view of the wound-care patch 100. Referring to FIGS. 1B-2 together, a window 120 is formed in a bottom face of the base layer 102. The fiber-optic strands 118 extend across the window 120. The wound-treatment portion 110 of the fluid conductor 108 (shown in FIG. 1A) is disposed over the window 120 above the fiber-optic strands 118. In a typical embodiment, the wound-care patch 100 is arranged such that the window 120 is positioned over the wound. A mesh 121 extends across the window 120 below the fiber-optic strands 118. In a typical embodiment, the mesh 121 prevents adhesion of wound tissue to either the fiber-optic strands 118 or the fluid conductor 108. A biocompatible skin adhesive (not shown) such as, for example, Tegaderm™, manufactured by 3M Company (hereinafter "Tegaderm"), is used to secure the edges of the wound-care patch 100 to skin surrounding the wound.

During operation, a vacuum pump (not explicitly shown) is coupled to the fluid port 114. Such an arrangement allows a relative vacuum to be applied to the wound via the fluid conductor 108. In addition, a source of ultra-violet light (not explicitly shown) is coupled to the fiber-optic strands 118. The ultra-violet light is emitted from the fiber-optic strands 118 into the wound. The ultraviolet light emitted from the fiber-optic strands 118 may be modulated to create various patterns of light, different intensities of light, and different durations of light such as, for example, pulsed emission of ultraviolet light. The ultraviolet light is capable of penetrating through several layers of skin to destroy infectious bacteria. According to exemplary embodiments, the ultraviolet light from fiber-optic strands 118 destroys a wide variety of microorganisms such as, for example, bacteria which causes skin infections. In addition, the ultraviolet light from the fiber-optic strands 118 improves wound healing along with cell and bone growth. Furthermore, the use of ultraviolet light in light therapy is safe, non-invasive, drug-free and therapeutic.

Still referring to FIGS. 1C-2, in various embodiments, a therapeutic agent, such as, for example, concentrated oxygen may be applied to the wound site via the port 114. In such embodiments, the port 114 may include two parallel lumen couplings to facilitate alternating application of the therapeutic agent and the relative vacuum. In various embodiments, the therapeutic agent may be thermally augmented prior to application to the wound area. In other embodiments, the therapeutic agent is not thermally augmented. Still referring to FIGS. 1C-2, in various embodiments, a radio frequency ("RF") antenna 122 is disposed around the window 120. In a typical embodiment, the RF antenna 122 comprises a wire 124. The wire 124 extends around a perimeter of the window 120. In a typical embodiment, the wire 124 is disposed such that, during use, the wire 124 is in close proximity to the wound. In various embodiments, the wire 124 is insulated to reduce risk of electric shock to a patient.

Still referring to FIGS. 1C-2, during operation, a pulsed radio-frequency ("RF") signal having a pulse frequency on the order of, for example 27 MHz, is transmitted to the RF antenna 122. In a typical embodiment, an amplitude of the pulsed RF signal is on the order of, for example, a fraction of a Watt. Such an amplitude is below a threshold where federal licensing is typically required. The RF antenna 122 receives the pulsed RF signal from a radio-frequency source and transmits the pulsed RF signal to a region in close proximity to the wound. Exposing the wound to the pulsed RF signal has been shown to be beneficial to healing by encouraging intracellular communication. In particular, pulsed RF signals have been shown to stimulate cellular bonding, and metabolism.

Figure 3:
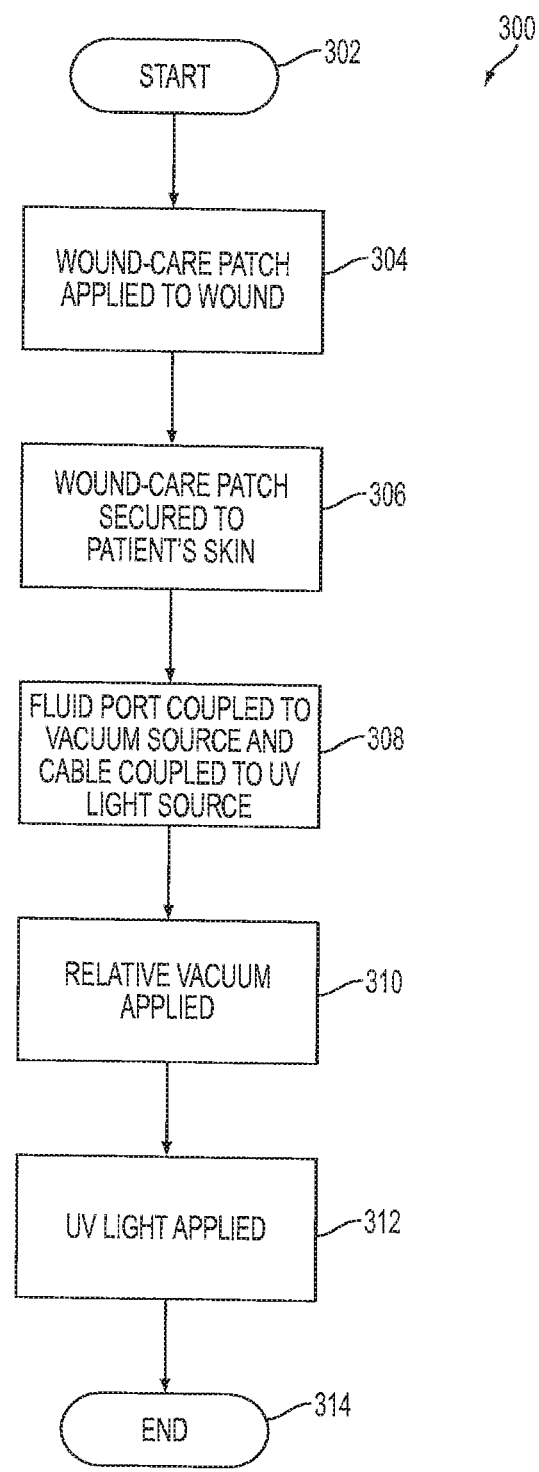
FIG. 3 is a flow diagram of a method for using the wound-care patch of FIG. 1 according to an exemplary embodiment.

FIG. 3 is a flow diagram of a process 300 for using the wound-care patch 100. The process 300 begins at step 302. At step 304, the wound-care patch 100 is applied to a wound.

At step 306, a biocompatible skin adhesive is used to secure the edges of the wound care patch 100 to a patient's skin surrounding the wound. At step 308, the fluid port 114 is coupled to a vacuum source and the fiber-optic cable 116 is connected to an ultraviolet light source. At step 310, a relative vacuum is applied to the fluid port 114. The relative vacuum is transmitted to the wound via the fluid conductor 108. In various embodiments, the relative vacuum facilitates removal of undesirable tissues from the wound such as, for example, dead tissue and foreign contaminants. In addition, the relative vacuum draws out fluid from the wound thereby increasing blood flow into the wound area. At step 312, ultraviolet light is supplied to the wound via the fiber-optic cable 116 and the fiber-optic strands 118. In a typical embodiment, the ultraviolet light is supplied to the wound area simultaneous with the application of the relative vacuum. In other embodiments, at least one of the ultraviolet light and the relative vacuum may be modulated or applied in various patterns and, thus, may not be simultaneous. The process 300 ends at step 314.

Figure 4A:
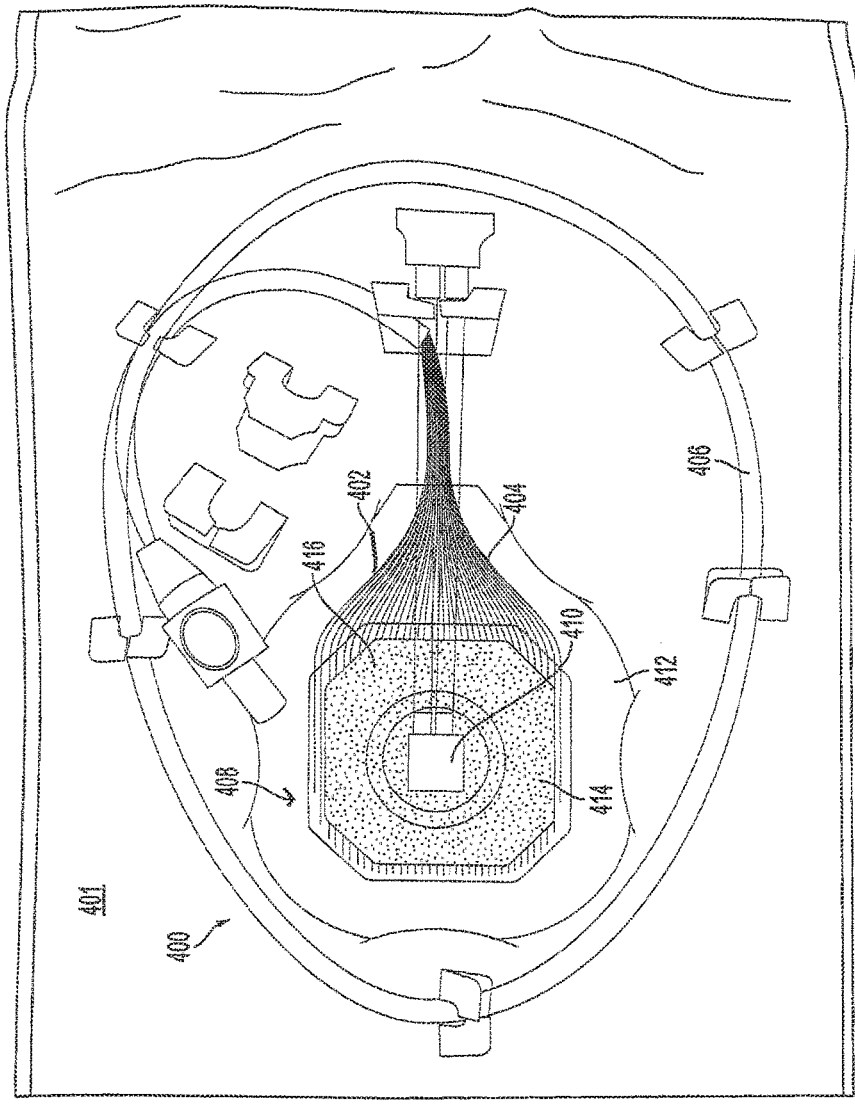
FIG. 4A is a top view of a package containing a wound-care assembly according to an exemplary embodiment.
Figure 4B:
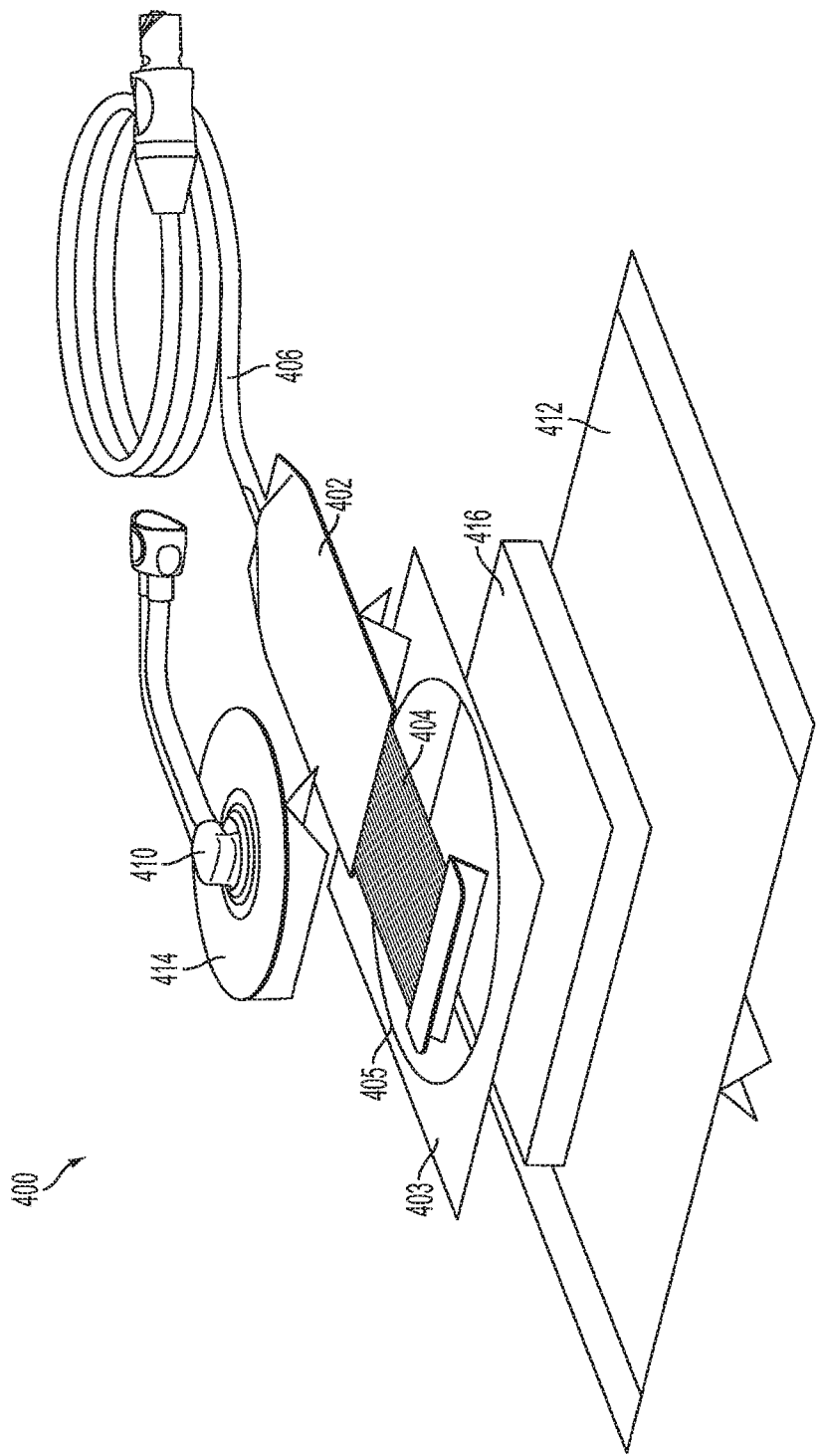
FIG. 4B is a an exploded view of the wound-care assembly of FIG. 4A.

FIG. 4A is a top view of a package 401 containing a wound-care assembly 400. FIG. 4B is an exploded view of the wound-care assembly 400. Referring to FIGS. 4A and 4B together, the wound-care assembly 400 includes a fiber-optic patch 402. The fiber-optic patch includes a plurality of fiber-optic strands 404. In a typical embodiment, the plurality of fiber-optic strands 404 are arranged in a generally flat side-by-side arrangement. The plurality of fiber-optic strands 404 are optically coupled to a fiber-optic cable 406. In a typical embodiment, the fiber-optic cable 406 is optically connectable to a source of ultraviolet light. The wound-care assembly 400 further includes a vacuum applicator 408. The vacuum applicator 408 includes a base layer 412 and a film layer 414. A fluid port 410 is formed in the film layer 414. A fluid conductor 416 is disposed beneath the fluid port 410 between the film layer 414 and the base layer 412. In a typical embodiment, the fluid conductor 416 is flexible, absorptive, and constructed of, for example, medical grade foam. In a typical embodiment, the fluid port 410 is connectable to a vacuum source. In a typical embodiment, the package 401 maintains the wound-care assembly in a sterile environment until use.

Still referring to FIGS. 4A and 4B, an RF layer 403 is disposed above the fiber-optic patch 402. The RF layer 403 includes an antenna 405 embedded therein. In a typical embodiment, the antenna 405 forms a loop around the wound. During operation, a pulsed radio-frequency ("RF") signal having a pulse frequency on the order of, for example 27 MHz, is transmitted to the antenna 405. In a typical embodiment, an amplitude of the pulsed RF signal is on the order of, for example, a fraction of a Watt. Such an amplitude is below a threshold where federal licensing is typically required. The antenna 405 receives the pulsed RF signal from a radio-frequency source and transmits the pulsed RF signal to a region in close proximity to the wound. Exposing the wound to the pulsed RF signal has been shown to be beneficial to healing by encouraging intracellular communication. In particular, pulsed RF signals have been shown to stimulate cellular bonding, and metabolism.

Figure 5A:
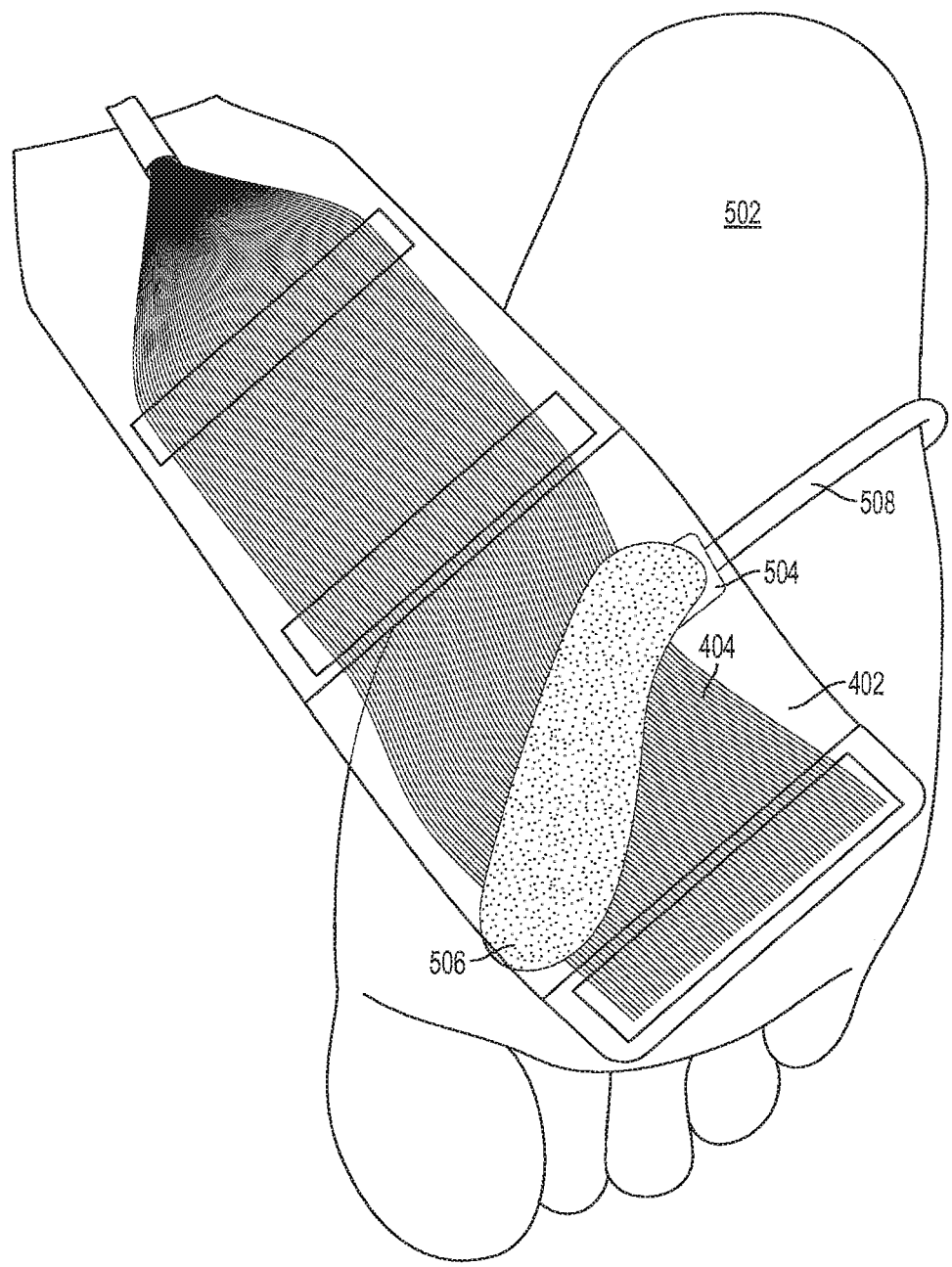
FIG. 5A is a bottom view of the wound-care assembly of FIG. 4 applied to a foot according to an exemplary embodiment.
Figure 5B:
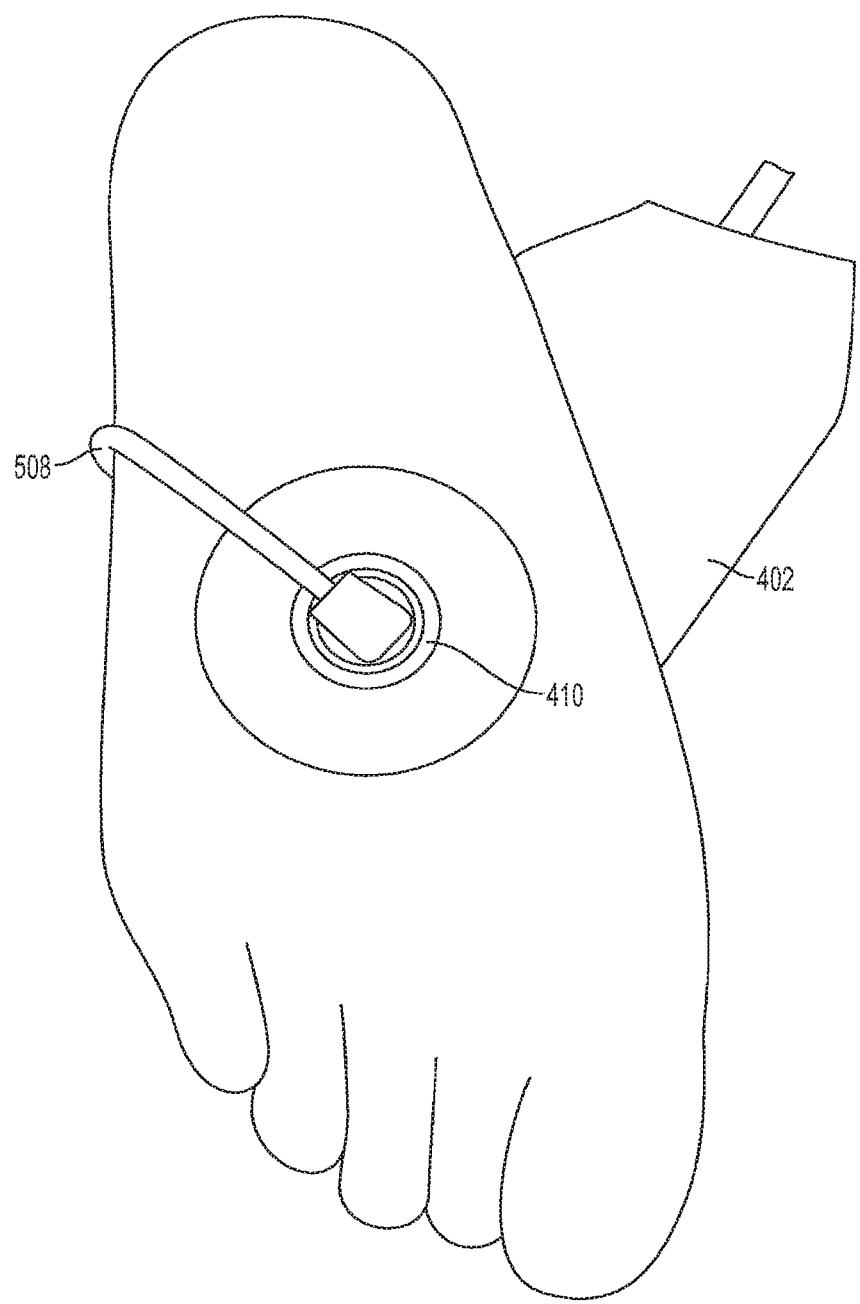
FIG. 5B is a top view of the wound-care assembly of FIG. 4 applied to a foot according to an exemplary embodiment.

FIG. 5A is a bottom view of the wound-care assembly 400 applied to a foot 502 of a patient. FIG. 5B is a top view of the wound-care assembly 400 applied to a foot 502 of a patient. As illustrated in FIGS. 5A-5B a wound 504 is present on the foot 502. The wound 504 is illustrated by way of example in FIG. 5 as being present on the foot 502; however, in other embodiments, the wound 504 may be disposed on any bodily region of the patient. The fiber-optic patch 402 is positioned over the wound 504 in such a manner that the fiber-optic strands 404 extend across a width of the wound 504. A fluid conductor 506 is shaped to approximately match a shape of the wound 504. In a typical embodiment, the fluid conductor 506 is flexible, absorptive, and constructed of, for example, medical grade foam. The fluid conductor 506 may cut or otherwise shaped to approximately match a size and shape of the wound 504. The fluid conductor 506 is positioned above the fiber-optic patch 402 and pressed downwardly into the wound 504 thereby pressing the fiber-optic strands 404 into contact with an interior surface of the wound 504. In various embodiments, a straw portion 508 may be fluidly coupled to the fluid conductor 506. In a typical embodiment, the straw portion 508 is constructed from a material similar to that of the fluid conductor 506. The straw portion 508 allows a relative vacuum to be applied to the wound 504, via the vacuum applicator 408, when the fluid port 410 is disposed a location remote to the wound 504 such as, for example, on a top of the foot 502. Such an arrangement is advantageous in situations where the wound 504 is located in a space-confined area such as, for example, a bottom of the patient's foot 502. The fiber-optic patch 402, the fluid conductor 506, and the straw portion 508 are secured in place via a biocompatible skin adhesive such as, for example, tegaderm.

Still referring to FIGS. 5A-5B, a small hole is formed in the biocompatible skin adhesive at a location where the vacuum applicator 408 is to be applied. In various embodiments, the vacuum applicator 408 is applied above the fluid conductor 506; however, in other embodiments, the vacuum applicator 408 may be applied to the straw portion 508. The vacuum applicator 408 is secured via a biocompatible skin adhesive such as, for example, tegaderm. In a typical embodiment, the wound-care assembly 400 facilitates flexible and modular construction for use on a wide variety of bodily areas and wound types.

Figure 6:
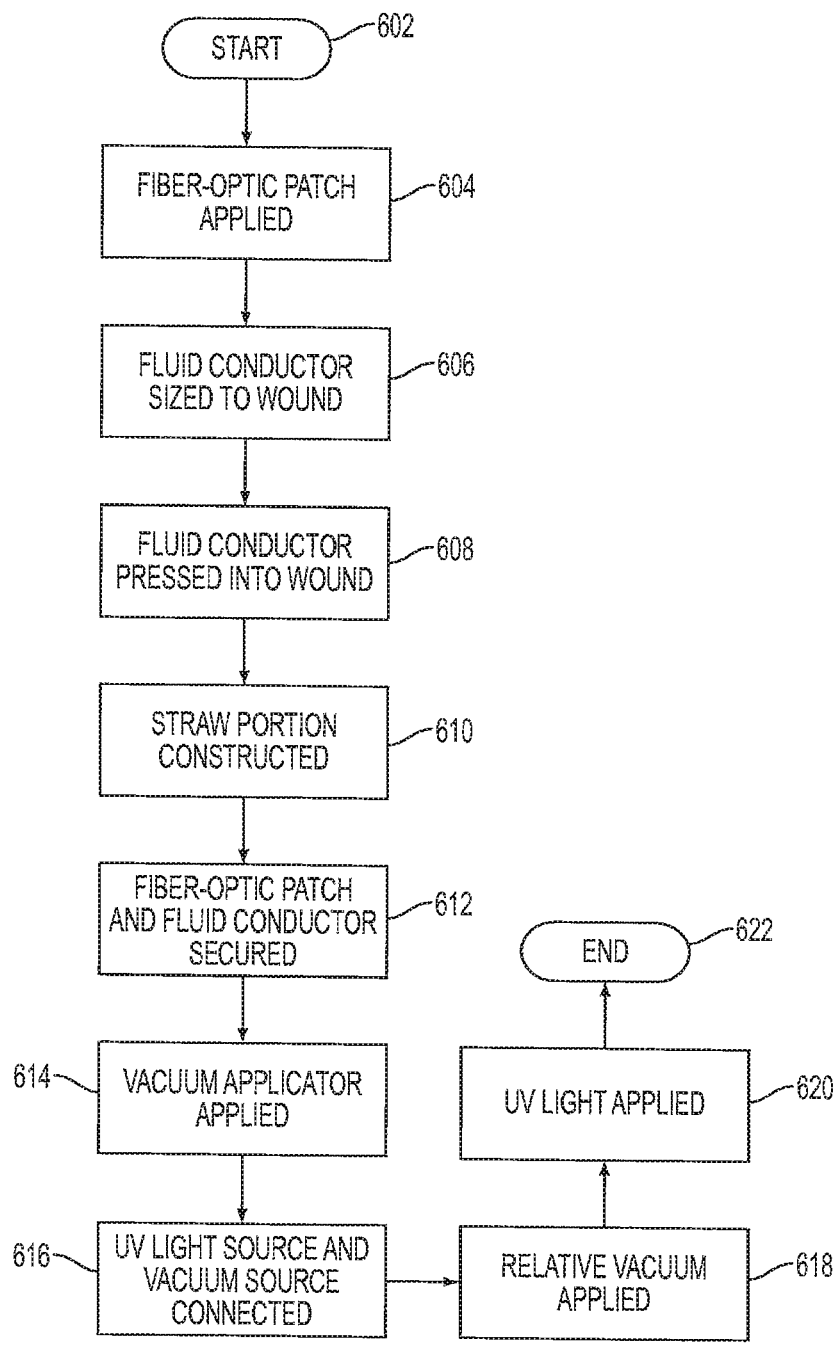
FIG. 6 is a flow diagram of a method for using the wound-care patch of FIG. 4 according to an exemplary embodiment.

FIG. 6 is a flow diagram of a process 600 for using the wound-care patch 400. The process 600 starts at step 602. At step 604, the fiber-optic patch 402 is placed over the wound 504. At step 606, the fluid conductor 506 is sized to approximately match a size and shape of the wound 504. At step 608, the fluid conductor 506 is pressed into the wound 504 above the fiber-optic patch 402. The fluid conductor 506 presses the fiber-optic strands 404 into contact with an inner surface of the wound 504. At step 610, a straw portion 508 is constructed in fluid communication with the fluid conductor 506. At step 612, the fiber-optic patch 402, the fluid conductor 506, and the straw portion 508 are secured with a biocompatible skin adhesive such as, for example, tegaderm. At step 614, the vacuum applicator is applied to at least one of the straw portion 508 or the fluid conductor 506.

Still referring to FIG. 6, at step 616, the fiber-optic cable 406 is connected to a source of ultraviolet light and the vacuum applicator 408 is fluidly coupled to a vacuum source. At step 618, a relative vacuum is applied to the wound 504 via the vacuum applicator 408, the fluid conductor 506, and, in some embodiments, the straw portion 508. In various embodiments, the relative vacuum facilitates removal undesirable tissues from the wound 504. At step 620, ultraviolet light is applied to the wound 504 via the fiber-optic cable 406, the fiber-optic patch 402, and the fiber-optic strands 404. In a typical embodiment, the ultraviolet light is supplied to the wound 504 simultaneous with the application of the relative vacuum. In other embodiments, at least one of the ultraviolet light and the relative vacuum may be modulated or applied in various patterns and, thus, may not be simultaneous. The process 600 ends at step 622.

Although various embodiments of the method and system of the present invention have been illustrated in the accompanying Drawings and described in the foregoing Specification, it will be understood that the invention is not limited to the embodiments disclosed, but is capable of numerous rearrangements, modifications, and substitutions without departing from the spirit and scope of the invention as set forth herein. It is intended that the Specification and examples be considered as illustrative only.

What is claimed is:

1. A method of utilizing a wound-care assembly, the method comprising:
    applying a fiber-optic patch to a wound;
    sizing a fluid conductor to fit inside the wound for fluid communication therewith;
    pressing the fiber-optic patch into contact with an inner surface of the wound via the fluid conductor;
    applying ultraviolet light to the wound via the fiber-optic patch; and
    applying a relative vacuum to the wound via the fluid conductor.

2. The method of claim 1, comprising securing the fluid conductor and the fiber-optic patch to the wound.

3. The method of claim 1, comprising applying a therapeutic agent to the wound via the fluid conductor.

4. The method of claim 3, comprising thermally augmenting the therapeutic agent.

5. The method of claim 1, comprising applying a pulsed radio-frequency (RF) signal to the wound via a radio-frequency antenna.

6. The method of claim 1, wherein the applying ultraviolet light comprises modulating the applied ultraviolet light.

7. The method of claim 1, wherein the applying a relative vacuum comprises fluidly coupling a vacuum applicator to a straw portion of the fluid conductor at a location distal to the wound.

8. The method of claim 1, comprising shaping the fluid conductor to approximately match a size and a shape of the wound.

9. The method of claim 1, wherein the applying a relative vacuum to a wound facilitates removal of undesirable materials from the wound.

10. The method of claim 1, wherein the fiber-optic patch comprises fiber-optic strands arranged in a flat side-by-side configuration.

\* \* \* \* \*